[12] United States Patent
Kinsky et al.

(10) Patent No.: US 10,589,045 B2
(45) Date of Patent: Mar. 17, 2020

(54) SMART OXYGENATION SYSTEM EMPLOYING AUTOMATIC CONTROL USING SPO2-TO-FIO2 RATIO

(71) Applicants: Board of Regents of the University of Texas System, Austin, TX (US); United States Government, as represented by the Secretary of the Army, Ft. Detrick, MD (US); University of Cincinnati, Cincinnati, OH (US)

(72) Inventors: Michael Kinsky, League City, TX (US); Rich Branson, Cincinnati, OH (US); George Kramer, Galveston, TX (US); Muzna Khan, Webster, TX (US); Jay Johanningman, Cincinnati, OH (US); Jose Salinas, San Antonio, TX (US); Nehemiah Liu, San Antonio, TX (US)

(*) Notice: Subject to any disclaimer, the term of this patent is extended or adjusted under 35 U.S.C. 154(b) by 335 days.

(21) Appl. No.: 15/725,172

(22) Filed: Oct. 4, 2017

(65) Prior Publication Data

US 2018/0099109 A1 Apr. 12, 2018

Related U.S. Application Data

(60) Provisional application No. 62/407,384, filed on Oct. 12, 2016.

(51) Int. Cl.
*A61M 16/00* (2006.01)
*A61M 16/10* (2006.01)
(Continued)

(52) U.S. Cl.
CPC .......... *A61M 16/024* (2017.08); *A61B 5/08* (2013.01); *A61B 5/14551* (2013.01);
(Continued)

(58) Field of Classification Search
CPC .............. A61M 16/00; A61M 16/0051; A61M 16/0057; A61M 16/022; A61M 16/024;
(Continued)

(56) References Cited

U.S. PATENT DOCUMENTS 6,675,798 B1 1/2004 Tyomkin et al.
8,554,298 B2 10/2013 Doyle et al.
(Continued)

OTHER PUBLICATIONS

R. Branson & B. Robinson, "Oxygen: When is More the Enemy of Good?" Intensive Care Medicine, 37:1-3 (2011).
(Continued)

*Primary Examiner* — Joseph D. Boecker
(74) *Attorney, Agent, or Firm* — Lewis & Reese, PLLC

(57) ABSTRACT

A system for assessing lung function in a patient is enclosed. The oxygen delivery system in the system (e.g., a ventilator or portable standalone system) preferably includes an oximeter sensor for receiving SpO2 from a patient. The assessing lung function in a patient includes an FiO2 adjust algorithm operable in logic circuitry in the ventilator that can control an oxygen fraction FiO2 provided to the patient in a closed loop fashion. In a preferred example, the algorithm controls FiO2 using the SpO2, but also displays a ratio of SpO2-to FiO2 ($S/_{CLC}F$) as a function of time. One or more $S/_{CLC}F$ ratio threshold may be used to allow the clinician and/or the algorithm to understand a degree of lung injury, and to allow the algorithm to adjust FiO2 appropriately. Preferably, the algorithm keeps SpO2 to a range of 88-95%.

40 Claims, 2 Drawing Sheets

(51) Int. Cl.

| | |
|---|---|
| *A61M 16/04* | (2006.01) |
| *A61M 16/06* | (2006.01) |
| *A61G 10/04* | (2006.01) |
| *A61B 5/1455* | (2006.01) |
| *A61B 5/00* | (2006.01) |
| *A61B 5/08* | (2006.01) |
| *A61M 16/12* | (2006.01) |

(52) U.S. Cl.
CPC .......... *A61B 5/4836* (2013.01); *A61B 5/4839* (2013.01); *A61G 10/04* (2013.01); *A61M 16/0051* (2013.01); *A61M 16/0057* (2013.01); *A61M 16/04* (2013.01); *A61M 16/06* (2013.01); *A61M 16/1005* (2014.02); *A61M 16/125* (2014.02); *A61M 2202/0208* (2013.01); *A61M 2205/18* (2013.01); *A61M 2205/3303* (2013.01); *A61M 2205/3569* (2013.01); *A61M 2205/502* (2013.01); *A61M 2230/205* (2013.01); *A61M 2240/00* (2013.01)

(58) Field of Classification Search
CPC ............ A61M 16/026; A61M 16/1005; A61M 16/125; A61M 2016/1025; A61M 2202/0208; A61M 2205/18; A61M 2205/50; A61M 2205/502; A61M 2230/005; A61M 2230/20; A61M 2230/205; A61M 2230/435; A61B 5/08; A61B 5/0833; A61B 5/14551; A61B 5/4836
See application file for complete search history.

(56) References Cited

U.S. PATENT DOCUMENTS

| | | | | |
|---|---|---|---|---|
| 9,364,623 | B2 | 6/2016 | Lellouche et al. | |
| 2003/0111078 | A1* | 6/2003 | Habashi ............... | A61M 16/024 128/204.18 |
| 2008/0295839 | A1* | 12/2008 | Habashi ............ | A61M 16/0051 128/204.22 |
| 2009/0320836 | A1* | 12/2009 | Baker, Jr. ............... | A61M 16/12 128/203.14 |
| 2012/0071729 | A1* | 3/2012 | Doyle ..................... | A61B 5/085 600/301 |
| 2014/0076317 | A1* | 3/2014 | Lotz ....................... | A61M 16/06 128/204.23 |
| 2015/0018648 | A1* | 1/2015 | Boyer ................ | A61M 16/1005 600/323 |
| 2015/0343160 | A1* | 12/2015 | Doyle ............... | A61M 16/0003 128/202.22 |
| 2017/0232214 | A1* | 8/2017 | Walsh ............... | A61M 16/0051 128/202.22 |
| 2018/0325463 | A1* | 11/2018 | Walsh ................. | A61B 5/0205 |
| 2018/0353718 | A1* | 12/2018 | Gale ....................... | A61B 5/083 |
| 2019/0365281 | A1* | 12/2019 | Orr .................... | A61B 5/14551 |

OTHER PUBLICATIONS

J. Johannigman et al., "Autonomous Control of Inspired Oxygen Concentration During Mechanical Ventilation of the Critically Injured Trauma Patient," J. Trauma Injury, Infection, and Critical Care, 66:386-392 (2009).
K. Burns et al., "Automating the Weaning Process with Advanced Closed-Loop Systems," Intensive Care Med., 34:1757-65 (2008).
CareFusion Corp., "ReVel® Ventilator: Taking Portability to New Heights," (2015) (downloaded from http:// www.carefusion.com/ Documents/ brochures/respiratory-care/mechanical-ventilation/ RC_ReVel-Ventilator_BR_EN.pdf).
R. Chatburn & E. Mireles-Cabodevila, "Closed-Loop Control of Mechanical Ventilation: Description and Classification of Targeting Schemes," Respiratory Care, 56(1):85-102 (2011).

W. Chen et al., "Clinical Characteristics and Outcomes are Similar in ARDS Diagnosed by Oxygen Saturation/FiO2 Ratio Compared with PaO2/FiO2 Ratio," Chest, 148:1477-83 (2015).
N. Ferguson et al., "The Berlin Definition of ARDS: An Expanded Rationale, Justification, and Supplementary Material," Intensive Care Medicine, 38:1573-82 (2012).
H. Gershengorn, "Hyperoxemia—Too Much of a Good Thing?" Critical Care, 18:556 (2014).
"Hamilton-G5: The Modular High-End Ventilation Solution," Hamilton Medical (2016)(downloaded from https:// www.hamilton-medical.com/ Products/ Mechanical-ventilators/HAMILTON-G5.html).
"Hamilton-G5: Technical Specifications www for SW Version 2.6x or Higher," Hamilton Medical (2016) (downloaded from https:// www.hamilton-medical.com/ Products/ Mechanical-ventilators/ HAMILTON-G5.html) (noting that Hamilton-G5 ventilator product includes closed-loop control and optional "numerical monitoring of SpO2/ FiO2 ratio as an approximation to PaO2/FiO2 ratio.").
http:// www.ardsnet.org/ files/ ventilator_protocol_2008-07.pdf (downloaded 2016).
M. Hutten et al., "Fully Automated Predictive Intelligent Control of Oxygenation (PRICO) in Resuscitation and Ventilation of Preterm Lambs," Pediatric Research, 1-7 (2015).
"Intellivent-ASV Bibliography", Hamilton Medical (2016) (downloaded from https ://www.hamilton-medical.com/dam/jcr:0fa98608-ecf8-4521-89b1-cb78d358fded/INTELLiVENT-ASV-bibliography-en-ELO20151135S.02.pdf).
P. Jernigan et al., "Portable Mechanical Ventilation with Closed-Loop Control of Inspired Fraction of Oxygen Maintains Oxygenation in the Setting of Hemorrhage and Lung Injury," J. of Trauma & Acute Care Surgery, 79(1):53-59 (2015) (suggesting an SpO2 of 94%).
M. Kinsky, "Smart Oxygen Monitors to Diagnose and Treat Cardiopulmonary Injuries," U.S. Army Award No. W81XWH-12-1-0598 (Annual Report, Oct. 2014) ("2014 Report").
M. Kinsky, "Smart Oxygen Monitors to Diagnose and Treat Cardiopulmonary Injuries," U.S. Army Award No. W81XWH-12-1-0598 (Annual Report, Oct. 29, 2015) ("2015 Report").
D. Martin & M. Grocott, "Oxygen Therapy in Anaesthesia: The Yin and Yang of O2," British J. of Anaesthesia, 111(6):867-871 (2013).
J. Mayordomo-Colunga et al., "Predicting Non-Invasive Ventilation Failure in Children from the SpO2/FiO2 (SF) ratio," Intensive Care Med., 39:1095-1103 (2013).
B. O'Driscoll et al., "BTS Guideline for Emergency Oxygen Use in Adult Patients," Thorax, 63(Suppl VI):vil-vi68 (2008) (downloaded from http:// thorax.bmj.com).
OxyNov France SARL, FreeO2 Ventilator (2016) (downloaded from http:// www.oxynov.com/en/).
T. Rice et al., "Comparison of the SpO2/FiO2 Ratio and the PaO2/FiO2 Ratio in Patients with Acute Lung Injury or ARDS," Chest, 132:410-17 (2014).
L. Rose, "Strategies for Weaning from Mechanical Ventilation: A State of the Art Review," Intensive & Critical Care Nursing, 31:189-195 (2015).
S. Satoshi et al., "Conservative Oxygen Therapy in Mechanically Ventilated Patients: A Pilot Before-and-After Trial," Critical Care Medicine, 42(6):1414-22 (2014) (suggesting an SpO2 of 90-92%).
C. Spada et al., "Oxygen Saturation/Fraction of Inspired Oxygen Ratio is a Simple Predictor of Noninvasive Positive Pressure Ventilation Failure in Critically Ill Patients," J. Critical Care, 26:510-16 (2011).
M. Wysocki et al., "Closed Loop Mechanical Ventilation," J. Clinical Monitoring & Computing, 28:49-56 (2014).
Zoll Medical Corp., 731 Family of Portable Ventilators (2016) (downloaded from https://www.zoll.com/ medical-products/ ventilators/).
N. Liu et al., "Closed-loop Control of FiO2 Rapidly Identifies Need for Rescue Ventilation and Reduces ARDS Severity in a Conscious Sheep Model of Burn and Smoke Inhalation Injury," Shock, Accepted for Publication (Jul. 2016).

* cited by examiner

SMART OXYGENATION SYSTEM EMPLOYING AUTOMATIC CONTROL USING SPO2-TO-FIO2 RATIO

CROSS REFERENCE TO RELATED APPLICATIONS

This is a non-provisional of U.S. Provisional Patent Application Ser. No. 62/407,384, filed Oct. 12, 2016, which is incorporated by reference in its entirety, and to which priority is claimed.

STATEMENT REGARDING GOVERNMENT INTERESTS

This work was supported in part by the following United States Government grants:

| Federal Agency: | Award No.: |
| --- | --- |
| U.S. Army | W81XWH-12-1-0598 |
| ONR | N00014-10-1-0252 |

The Government may have certain rights in this invention.

FIELD OF THE INVENTION

The present invention relates generally to oxygen delivery systems for providing oxygenation to a patient.

BACKGROUND

Mechanical ventilation is a treatment that supports and assists breathing in patients with impaired lung function. It is used to treat a wide range of indications, including acute respiratory distress syndrome (ARDS), apnea, asthma, chronic obstructive pulmonary disease (COPD), acute respiratory acidosis, tachypnea, respiratory distress, respiratory support of premature neonates, hypoxemia, cardiogenic and non-cardiogenic pulmonary edema, and drug-induced or neurological impairments of the diaphragm. Mechanical ventilators are available for both acute and non-acute settings (e.g., intensive care, neonatal, portable units for emergency transport and home use, and sleep apnea devices).

Invasive ventilation provides oxygen using an artificial airway, e.g., an endotracheal or tracheostomy tube. Noninvasive ventilation (NIV) provides oxygen through an external interface, e.g., a mouth or nose piece, or a face mask. Ventilators can provide room air and/or supplemental oxygen. The fraction of oxygen in the inspired air (FiO2) can range from 0.21 (21%) as in room air, or up to 1.0 (100%) oxygen in critical cases. Ventilators can also assist breathing by providing positive pressure in a continuous or intermittent fashion (e.g., positive end-expiratory pressure (PEEP) and continuous positive airway pressure (CPAP)).

Because the goal of ventilation is to ensure sufficient oxygenation of the body, various measurements have been used to assess the sufficiency of the intervention. If sufficient oxygenation is achieved, the physician may choose to withdraw or wean the patient from ventilation (e.g., by extubation, or by removing NIV). By contrast, if insufficient oxygenation is detected, the physician may choose to escalate to a more aggressive means of respiratory support (e.g., from NIV to intubation). While initiating mechanical ventilation is often a life-saving intervention, it carries risks and complications, especially with prolonged use, including barotrauma, ventilator-associated lung injury (VALI), diaphragm atrophy, and increased mucus potentially leading to pneumonia. Accordingly, it is desirable to apply mechanical ventilation only for the duration and intensity that is medically necessary.

To measure lung oxygenation and lung injury severity, clinicians have historically relied on the ratio of the partial pressure of oxygen in the arterial blood (PaO2) and the fraction of inspired oxygen (FiO2), i.e., a PaO2/FiO2 ratio, or P/F for short). Arterial blood is the blood that leaves the lungs after oxygenation, and therefore measuring PaO2 requires an invasive arterial blood sample (invasive stick of the artery or catheter) and specialized equipment (blood gas machine). Thus, P/F can only be obtained in skilled facilities with clinical staff (physicians and respiratory therapists). Another limitation is that PaO2 measures oxygen dissolved in blood plasma rather than oxygen saturation of blood hemoglobin (SpO2), which more directly reflects oxygen delivery to body tissues.

FIG. 1 shows an oxygen dissociation curve, which shows the nonlinear relationship between SpO2 and PaO2. This curve depends on the fraction of oxygen gas delivered (FiO2) by a ventilator, or the amount of oxygen delivered in liter-per-minute by air or mask in a portable, standalone system. (For simplicity, all oxygen delivery systems are herein described as delivering oxygen as measured in "FiO2."). In FIG. 1, normal arterial blood values of SpO2 and PaO2 are shown assuming breathing room air with an FiO2 of 0.21 (21%). If the lungs are damaged, SpO2 will be less than the normal SpO2 range of 95 to 99%. Using oxygen, positive pressure (mechanical) ventilation (e.g. increased tidal volume and respiratory rate) or positive expiratory pressure (PEEP), the caregiver can often increase SpO2 to the within the normal range, but in severely diseased lungs, it may not be possible to reach a normal SpO2 level.

Increasing the fraction of oxygen (FiO2) can drastically increase PaO2, up to hundreds of mmHg. But this has very little added benefit to SpO2, which plateaus around 95%. Thus, when a patient is ventilated, a SpO2 of greater than 95% does not accurately indicate PaO2. In practice, excessive FiO2 is often delivered out of an abundance of caution under the presumption that hypoxemia presents a greater risk that hyperoxemia. See H. Gershengorn, "Hyperoxemia—Too Much of a Good Thing?" Critical Care, 18:556 (2014); R. Branson & B. Robinson, "Oxygen: When is More the Enemy of Good?" Intensive Care Medicine, 37:1-3 (2011).

Similarly to P/F, clinicians have used the SpO2/FiO2 ratio (S/F) to assess oxygenation, and use of S/F has been validated to assess prognosis and severity of acute lung injury. T. Rice et al., "Comparison of the SpO2/FiO2 Ratio and the PaO2/FiO2 Ratio in Patients with Acute Lung Injury or ARDS," CHEST, 132:410-17 (2014); W. Chen et al., "Clinical Characteristics and Outcomes are Similar in ARDS Diagnosed by Oxygen Saturation/FiO2 Ratio Compared with PaO2/FiO2 Ratio," CHEST, 148:1477-83 (2015); "Hamilton-G5: Technical Specifications for SW Version 2.6x or Higher," Hamilton Medical (2016) (downloaded from https://www.hamilton-medical.com/Products/Mechanical-ventilators/HAMILTON-G5.html) (noting that Hamilton-G5 ventilator product includes closed-loop control and optional "numerical monitoring of SpO2/FiO2 ratio as an approximation to PaO2/FiO2 ratio."). S/F has also been used to identify and/or predict NIV (non-invasive ventilation) failure in adult and pediatric patients, i.e., as an indicator that more aggressive intervention, e.g., intubation, is needed. C. Spada et al., "Oxygen Saturation/Fraction of Inspired Oxygen Ratio is a Simple Predictor of Noninvasive Positive Pressure Ventilation Failure in Critically Ill Patients," J. Critical Care, 26:510-16 (2011); J. Mayordomo-Colunga et al., "Predicting Non-Invasive Ventilation Failure in Children from the SpO2/FiO2 (SF) ratio," Intensive Care Med., 39:1095-1103 (2013); U.S. Pat. No. 8,554,298.

Unlike PaO2, SpO2 can be measured noninvasively, for example, by pulse oximetry. Thus, SpO2 can be measured in less specialized settings, and can be measured more frequently, or even continuously, to provide rapid feedback of oxygenation status. Such data could be automatically incorporated into an electronic medical record. And because SpO2 is a measure of blood hemoglobin saturation (rather than plasma oxygen concentration), it is a direct reflection of the oxygen-carrying capacity of the blood. However, only a few commercially available ventilators include an integrated pulse oximeter to measure SpO2. See, e.g., "Hamilton-G5: The Modular High-End Ventilation Solution," Hamilton Medical (2016) (downloaded from https://www.hamilton-medical.com/Products/Mechanical-ventilators/HAMIL-TON-G5.html); CareFusion Corp., "ReVel® Ventilator: Taking Portability to New Heights," (2015) (downloaded from http://www.carefusion.com/Documents/brochures/respiratory-care/mechanical-ventilation/RC_ReVel-Ventilator_BR_EN.pdf); Zoll Medical Corp., 731 Family of Portable Ventilators (2016) (downloaded from https://www.zoll.com/medical-products/ventilators/);

The S/F ratio closely approximates the P/F ratio under many conditions. Accordingly, guidelines from the National Institutes of Health's National Heart, Lung, and Blood Institute (NIH-NHLBI) state that for ARDS treatment, the least amount of oxygen (FiO2) should be used to maintain SpO2 at 88-95%, which is equivalent to a PaO2 of 55-80 mmHg, as shown by the region in FIG. 1 bounded by the dotted lines. See http://www.ardsnet.org/files/ventilator_protocol_2008-07.pdf (downloaded 2016). A SpO2 of 88-95% corresponds to a relatively steep portion of the oxygen dissociation curve of FIG. 1 where PaO2 is also changing significantly. Beyond that range, i.e., increasing PaO2 above 80 mmHg, makes little difference in SpO2. Other literature consistent with these NIH-NHLBI ARDS guidelines also suggests maintaining SpO2 within this range to decrease oxygen consumption. P. Jernigan et al., "Portable Mechanical Ventilation with Closed-Loop Control of Inspired Fraction of Oxygen Maintains Oxygenation in the Setting of Hemorrhage and Lung Injury," J. of Trauma & Acute Care Surgery, 79(1):53-59 (2015) (suggesting an SpO2 of 94%); S. Satoshi et al., "Conservative Oxygen Therapy in Mechanically Ventilated Patients: A Pilot Before-and-After Trial," Critical Care Medicine, 42(6):1414-22 (2014) (suggesting an SpO2 of 90-92%).

Despite the above-referenced NIH-NHLBI guidelines to maintain SpO2 at 88-95%, in practice, SpO2 is frequently maintained at very high levels (e.g., greater than 95%, greater than 98%, or even at or nearly 100%). Setting SpO2 above 95% can mask the diagnostic value of S/F and results in several clinical consequences. First, at very high SpO2, the SpO2 and PaO2 become discordant, because higher FiO2 will raise PaO2 with little effect on SpO2. Second, at very high SpO2, it may take several additional minutes to recognize a change in lung function. Finally, in addition to the delay in recognizing a change in lung function, there is also a delay of several minutes to hours for the caregiver to adjust the ventilation settings in response to the change in lung function.

The art has provided Closed Loop Control (CLC) to automatically adjust ventilation parameters (e.g., FiO2, positive pressure, etc.) in response to feedback from the system to maintain oxygenation targets. M. Wysocki et al., "Closed Loop Mechanical Ventilation," J. Clinical Monitoring & Computing, 28:49-56 (2014); R. Chatburn & E. Mireles-Cabodevila, "Closed-Loop Control of Mechanical Ventilation: Description and Classification of Targeting Schemes," Respiratory Care, 56(1):85-102 (2011).

Closed Loop Control of FiO2 (CLC-FiO2) automatically adjusts the fraction of inspired oxygen (FiO2) delivered in response to changes in ventilation parameters to maintain target values for SpO2. An example of a system 10 in which this occurs is shown in FIG. 2. System 10 includes an oxygen delivery system 12 that provides an oxygen fraction FiO2 to a patient 14. Oxygen delivery system can comprise both ventilators (e.g., devices equipped to be capable of providing mechanical breathing assistance) and portable "stand alone" oxygen delivery devices that simply provide O2. Such oxygen can be provided to the patient through a mask (e.g., face mask, mouth piece, nose piece, nasal cannula), tube (e.g., an endotracheal or tracheostomy tube), or chamber (e.g., a hyperbaric chamber) 16. The patient wears an oximeter sensor 18, usually on a fingertip, which detects SpO2. This SpO2 reading is reported back to an FiO2 adjust algorithm 20 in the oxygen delivery system 12, which can operate in logic circuitry (e.g., a microprocessor, microcontroller, DPS, FPGA, or similar logic device) in the oxygen delivery system 12. System 10 further includes a display monitor 22, which may be used to provide visual indication of operation of the oxygen delivery system 12 to a clinician. Display monitor 22 may be incorporated within the body of the oxygen delivery system 12 as is common, or may be a self-standing display monitor connected to the oxygen delivery system via a cable. Oxygen delivery system 12 may comprise a mechanical ventilator, a portable mechanical ventilator, or a neonatal mechanical ventilator.

Depending on the SpO2 reading, the FiO2 adjust algorithm 20 can either increase or decrease the oxygen fraction FiO2 to keep SpO2 within a desired range, such as 90-95%. For example, if SpO2 falls, the system can automatically increase the FiO2 delivered to maintain SpO2 within the target range. Conversely, as SpO2 improves, the system 10 can automatically decrease the FiO2 delivered to facilitate weaning from invasive ventilation. FiO2 adjust algorithm 20 can also operate to adjust FiO2 up or down depending on a rate of change of SpO2. See Chatburn & Mireles-Cabodevila, cited above. Furthermore, many Closed Loop systems include will provide 100% FiO2 if SpO2 falls below 88% for a certain amount of time. Tight control of SpO2 by using CLC-FiO2 results in less hypoxia, less hyperoxia, and less FiO2 use. J. Johannigman et al., "Autonomous Control of Inspired Oxygen Concentration During Mechanical Ventilation of the Critically Injured Trauma Patient," J. TRAUMA Injury, Infection, and Critical Care, 66:386-392 (2009); Wysocki, cited above. Exemplary portable oxygen delivery systems utilizing CLC-FiO2 and integrated pulse oximetry include those described in U.S. Pat. Nos. 9,364, 623 and 6,675,798.

Using CLC-FiO2 to maintain a target SpO2 has been used for:
    automatic weaning from invasive ventilation for adult and pediatric patients. K. Burns et al., "Automating the Weaning Process with Advanced Closed-Loop Systems," Intensive Care Med., 34:1757-65 (2008); L. Rose, "Strategies for Weaning from Mechanical Ventilation: A State of the Art Review," Intensive & Critical Care Nursing, 31:189-195 (2015);

remote medical care in austere environment. Johannigman, cited above;

maintaining oxygenation in lung injury. Jernigan, cited above, (noting that "a portable ventilator modified with a CLC algorithm, which uses feedback from pulse oximetry (SpO2) and FiO2 trends to adjust FiO2 and maintain a target SpO2 of 94%."); and automated oxygen supplementation for neonatal intensive care unit (NICU). M. Hutten et al., "Fully Automated Predictive Intelligent Control of Oxygenation (PRICO) in Resuscitation and Ventilation of Preterm Lambs," Pediatric RESEARCH, 1-7 (2015).

DETAILED DESCRIPTION

Figure 1:
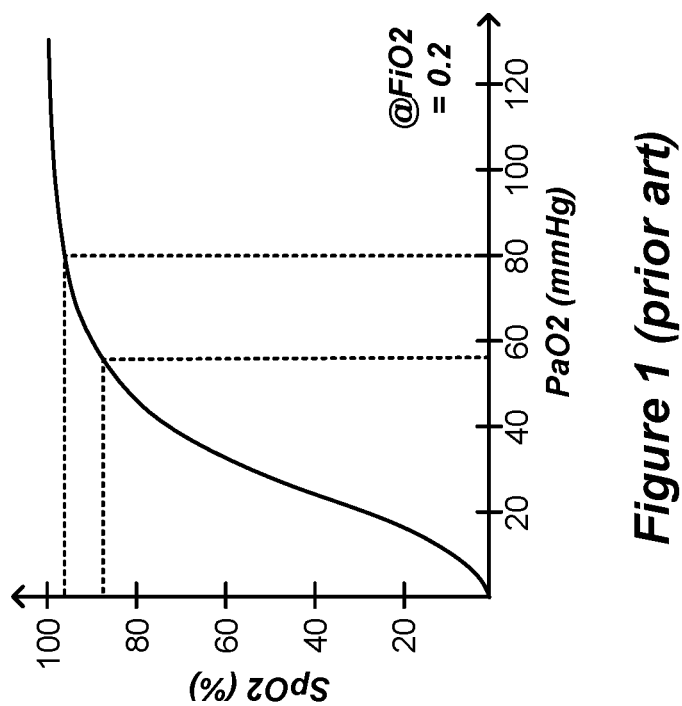
FIG. 1 shows a SpO2/PaO2 oxygen dissociation curve, in accordance with the prior art.
Figure 2:
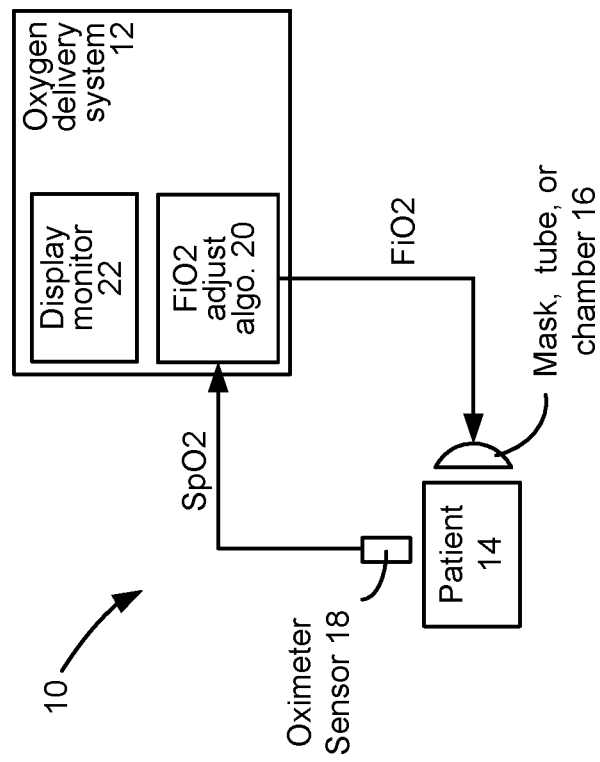
FIG. 2 shows a prior art ventilation system, including an oximeter sensor to report SpO2 to the ventilator, in accordance with the prior art.

Existing ventilation systems adjust FiO2 in a closed loop fashion with the goal of maintaining SpO2 within a set range. Closed Loop Control has also been used in conjunction with the S/F ratio described earlier. See, e.g., M. Kinsky, "Smart Oxygen Monitors to Diagnose and Treat Cardiopulmonary Injuries," U.S. Army Award Number W81XWH-12-1-0598 (Annual Report, October 2014) ("2014 Report"). The 2014 Report discloses use of closed loop ventilation systems similar to those shown in FIG. 2 to diagnose and treat lung injury, and identifies SpO2:CLC-FiO2—i.e., using the $S/_{CLC}F$ ratio to control FiO2 in a closed loop fashion—as a "new vital sign." The 2014 report further identifies thresholds for $S/_{CLC}F$ that indicate adequate pulmonary function and pulmonary distress, and suggest that a display e.g., the display monitor 22 of FIG. 2 should display the variables over time for SpO2, CLC-FIO2, and its ratio [$S/_{CLC}F$].

Thus, the 2014 Report and subsequent reports show the promise of using the S/F ratio as a variable to control FiO2 in a closed loop. See also M. Kinsky, "Smart Oxygen Monitors to Diagnose and Treat Cardiopulmonary Injuries," U.S. Army Award Number W81XWH-12-1-0598 (Annual Report, Oct. 29, 2015) ("2015 Report").

However, in the inventors' opinion, mere use of the $S/_{CLC}F$ ratio to control FiO2 administered to the patient may not always result in ideal oxygenation therapy. In part this is because an S/F ratio by itself is agnostic as to the value of SpO2, as well as its rate of change.

Figure 3:
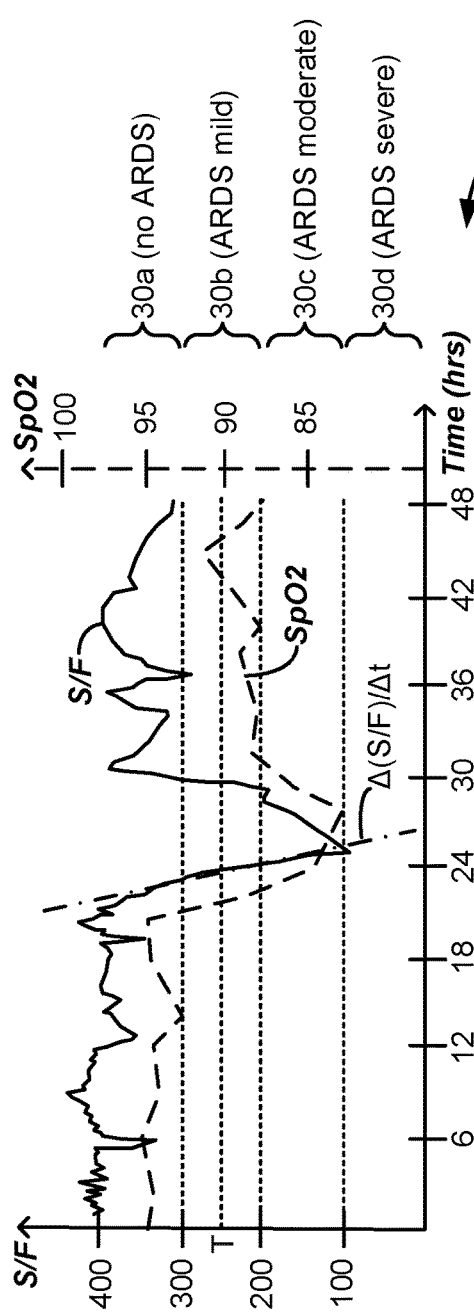
FIG. 3 shows a display of an improved ventilation system, displaying an SpO2/FiO2 (S/F) ratio, SpO2, and a rate of change of S/F, in accordance an example of the invention.

FIG. 3 shows an example of an $S/_{CLC}F$ ratio as may be displayed by an oxygen delivery system 12 over time on its monitor display 22. As shown, the $S/_{CLC}F$ ratio is classified into different regions indicating different levels of ARDS severity, with $S/_{CLC}F$>300 indicating no apparent ARDS, or generally speaking normal lung function (30a); 200-300 indicating mild ARDS (30b); 100-200 indicating moderate ARDS (30c); and $S/_{CLC}F$<100 indicating severe ARDS (30d). Thus, different $S/_{CLC}F$ thresholds of 300, 200, and 100 are identified, and are adapted from the Berlin criteria. See N. Ferguson et al., "The Berlin Definition of ARDS: An Expanded Rationale, Justification, and Supplementary Material," Intensive Care Medicine, 38:1573-82 (2012). An $S/_{CLC}F$ ratio of 250 (in the middle of the mild ARDS range), can generally be considered as a threshold (T) requiring a change of FiO2 in a closed loop system, although other thresholds (at $S/_{CLC}F$=100, 200, 30, etc.) could also be used. One or more alerts (either graphical alerts on the display monitor 22, or audible alerts) may be issued by the oxygen delivery system 112 when one or more S/F thresholds are crossed.

Figure 4:
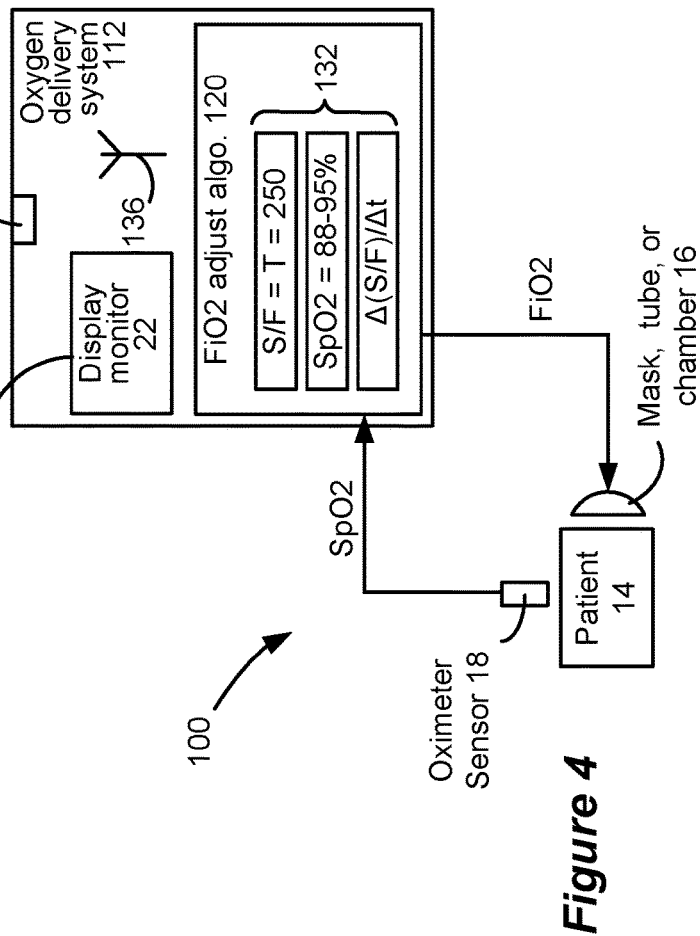
FIG. 4 shows the improved ventilation system, which in conjunction with an FiO2 adjust algorithm can control FiO2 provided to the patient in accordance to achieve an appropriate SpO2 range, such as 88-95%, in accordance with an example of the invention.

FIG. 4 shows a system 100 useable to provide the display shown in FIG. 3, and which includes an improved FiO2 adjustment algorithm 120 capable of adjusting FiO2 in a close loop fashion depending on SpO2 with the goal of keeping SpO2 within a given range (e.g., 88-95%), which as noted above can provide a sufficient but minimal amount of oxygen, and therefore keep FiO2 to a minimum during closed loop control. See http://www.ardsnet.org/files/ventilator_protocol_2008-07.pdf (downloaded 2016).

The algorithm 120 also calculates the $S/_{CLC}F$ ratio, and tracks it versus one or more $S/_{CLC}F$ thresholds, such as $S/_{CLC}F$=T=250, and the $S/_{CLC}F$ ratio is preferably graphed on display monitor 22 as a function of time. The $S/_{CLC}F$ ratio can be calculated using SpO2 as reported by the oximeter sensor, and using the current value of FiO2 being provided by the closed loop control oxygen delivery system 112. $S/_{CLC}F$ thresholds can be stored in memory 132 in the ventilator 112. When $S/_{CLC}F$ falls below a threshold (e.g., T=250) as shown in FIG. 3, an alarm can issue for instance. In the example shown, it is seen that when SpO2 falls below its desired range (e.g., <88%), the S/F ratio is also low. As the algorithm increases FiO2 (e.g., from 0.21 to 0.5) to try and increase SpO2, both SpO2 and the $S/_{CLC}F$ ratio begin to rise to acceptable levels.

The FiO2 adjustment algorithm 120 in an alternative example also adjusts FiO2 in accordance with the $S/_{CLC}F$ ratio as well as the current value of SpO2. See http://www.ardsnet.org/files/ventilator_protocol_2008-07.pdf (downloaded 2016). Because FiO2 adjustment algorithm 120 considers both the $S/_{CLC}F$ ratio and SpO2 when adjusting FiO2, the algorithm may need to balance competing interests, and generally with the conservative goal as always ensuring that the patient has sufficient oxygen. For example, if the $S/_{CLC}F$ ratio is sufficient (e.g., 300), but SpO2 is low (e.g., 87%), algorithm 120 will preferably increase FiO2. Likewise, if the $S/_{CLC}F$ ratio is low (e.g., 280), but SpO2 is sufficient (e.g., 90%), algorithm 120 may again preferably increase FiO2. Again, conservative automatic control of FiO2 is desired.

FiO2 adjustment algorithm 120 may also along with the $S/_{CLC}F$ ratio takes into account the rate by which the $S/_{CLC}F$ ratio may be changing ($\Delta(S/_{CLC}F)/\Delta t$), which parameter may be computed and stored in memory 132. Rate of change of $S/_{CLC}F$ can be different from patient to patient, and can be significant as to how aggressively the algorithm 120 should adjust FiO2. For example, as shown in FIG. 3, the patient begins to experience significant impairment in lung function at around 23 hours (when $S/_{CLC}F$ decreases below 300). In this example, the rate of change of $S/_{CLC}F$ is relatively sharp, suggesting that FiO2 might perhaps be increased by a significant amount (e.g., to FiO2=0.7). Were $S/_{CLC}F$ decreasing more slowly, FiO2 might be changed to a lesser amount (e.g., to FiO2=0.35).

In short, in the disclosed system 100, the FiO2 adjustment algorithm 120 in the oxygen delivery system 112 preferably uses SpO2 as a closed loop variable to adjust FiO2, with the goal of keeping SpO2 with a desired range (88-95%), and may additionally use the $S/_{CLC}F$ ratio and the rate of change of the $S/_{CLC}F$ ratio (($\Delta(S/_{CLC}F)/\Delta t$)) to control FiO2 provided to the patient as well. If both $S/_{CLC}F$ and $\Delta(S/_{CLC}F)/\Delta t$ are considered along with SpO2, FiO2 adjustment algorithm 120 can balance or weigh these parameters as appropriate to provide the desired closed loop control to achieve the desired SpO2 range.

As well as increasing the amount of oxygen provided to the patient (FiO2) using SpO2, and optionally the $S/_{CLC}F$ ratio and the rate of change of that ratio, the FiO2 adjust algorithm 120 could automatically escalate intervention in other ways, such as by increasing or initiating PEEP, increasing or initiate positive or negative pressure, increasing tidal volume, or taking other actions that affect the manner in which the inspired oxygen is provided to the patient, assuming that the oxygen delivery system 112 in question allows such variables to be changed. Further, the FiO2 adjustment algorithm may also indicate to the clinician (e.g., on the display monitor or audibly), that other interventions are warranted, such intubation. Likewise, FiO2 adjustment algorithm may also deescalate the intervention by automatically reducing or stopping these inspiration parameters, and by indicating extubation.

In a preferred example, the logic circuitry in which FiO2 adjustment algorithm 120 operates in the oxygen delivery system 112 provides data to the display monitor 22 so that it may be displayed to a clinician. In a preferred example, the $S/_{CLC}F$ ratio is graphed over time as is SpO2, as shown in FIG. 3. Various $S/_{CLC}F$ thresholds (e.g., 100, 200, 250, 300) may also be displayed, and may perhaps be highlighted with different colors to highlight the different regions of ARDS severity (30a-30d). Additionally, the rate of change of the $S/_{CLC}F$ ratio—$\Delta(S/_{CLC}F)/\Delta t$—may also be calculated and graphed as a function of time, although this is not shown in FIG. 3. Such graphed parameters on the display monitor 22 may be overlaid, or graphed as separate non-overlapping traces. The current values for each of these parameters may also be shown on the display monitor 22. Finally, the FiO2 being provided by the oxygen delivery system 112 may also be graphed as a function of time, and/or its current values shown, although again this isn't shown in FIG. 3. Display of one or more of these parameters will assist the clinician in understanding how the FiO2 adjustment algorithm 120 is operating, and how the patient's oxygenation therapy is progressing.

These parameters may also be transmittable from the oxygen delivery system 112 to other external devices. In the regard, the oxygen delivery system 112 can include a port 134 for receiving a cable to transmit parameters through the cable to an external device such as a clinician's computer, personal computer, lap top computer, tablet, cell phone, etc., or other computer system operable at a hospital handling electronic medical records (EMRs) for example. Alternatively, the oxygen delivery system 112 can include an antenna 136 and associated transceiver circuitry to wirelessly transmit such parameters to such devices.

It should be understood that while the disclosed ventilator system 100 has been described as measuring SpO2 continuously, calculating $S/_{CLC}F$ and the rate of change of $S/_{CLC}F$ continuously, and adjusting FiO2 continuously, this does not imply that the such measuring, calculating, and adjusting occur at all times without stopping. Instead, continuous in this context means on some sort of time scale which may be periodic or which can occur as necessary.

The improved oxygen delivery system 112 and FiO2 adjust algorithm 120 is expected to be useful with patients having acute respiratory distress syndrome (ARDS); patients having chronic obstructive pulmonary disease (COPD); patients having congestive heart failure (CHF); neonate patients; patients that have suffered a traumatic injury, such as in a military field or as a result of a mass causality; patients being triaged (e.g., in an emergency room); patients that have recently been extubated (e.g., as a monitor for extubation failure); and patients that have been anesthetized (e.g., use in post-anesthesia care unit (PACU)).

Although particular embodiments of the present invention have been shown and described, it should be understood that the above discussion is not intended to limit the present invention to these embodiments. It will be obvious to those skilled in the art that various changes and modifications may be made without departing from the spirit and scope of the present invention. Thus, the present invention is intended to cover alternatives, modifications, and equivalents that may fall within the spirit and scope of the present invention as defined by the claims.

What is claimed is:

1. A system for providing oxygenation to a patient, comprising:
   an oxygen delivery system configured to continually provide a fraction of inspired oxygen (FiO2) to the patient;
   an oximeter configured to continually measure a percentage oxygen saturation of blood hemoglobin (SpO2) of the patient and report the measured SpO2 to the oxygen delivery system;
   logic circuitry configured to continually calculate a ratio of the measured SpO2 to the provided FiO2 ($S/_{CLC}F$ ratio);
   an algorithm operable in the logic circuitry and configured to continually adjust the FiO2 provided to the patient given the currently-measured SpO2 and the currently-measured $S/_{CLC}F$ ratio to try and maintain SpO2 within a desired range; and
   a display monitor, wherein the logic circuitry is configured to cause the display monitor to display the $S/_{CLC}F$ ratio as a function of time.

2. The system of claim 1, wherein the logic circuitry is further configured to cause the display monitor to display one or both of measured SpO2 and a calculated rate of change of the $S/_{CLC}F$ ratio as a function of time.

3. The system of claim 2, wherein the display monitor is integrated within a body of the oxygen delivery system.

4. The system of claim 1, wherein the desired SpO2 range comprises 88% to 95%.

5. The system of claim 1, wherein the logic circuitry is configured to issue an alert when the $S/_{CLC}F$ ratio falls below a predetermined threshold.

6. The system of claim 5, wherein the predetermined threshold comprises 250.

7. The system of claim 1, further comprising a tube, wherein the FiO2 is provided to the patient by the tube.

8. The system of claim 1, further comprising a mask, wherein the FiO2 is provided to the patient by the mask.

9. The system of claim 1, further comprising a chamber, wherein the FiO2 is provided to the patient by the chamber.

10. The system of claim 1, wherein the oxygen delivery system is mechanical.

11. The system of claim 1, wherein the oxygen delivery system is configured to be portable and standalone.

12. The system of claim 1, wherein the oxygen delivery system comprises a ventilator.

13. The system of claim 1, wherein the oxygen delivery system is configured to home oxygen therapy use.

14. The system of claim 1, wherein the algorithm is further configured to continually adjust a pressure at which the FiO2 is provided to the patient.

15. The system of claim 1, further comprising an antenna, wherein the logic circuitry is configured to cause the antenna to transmit to an external device any one or more of SpO2, the $S/_{CLC}F$ ratio, and a calculated rate of change of the $S/_{CLC}F$ ratio, as a function of time.

16. The system of claim 1, wherein FiO2 is provided at an oxygen flow rate.

17. A method for assessing lung function in a patient, comprising:
    providing a fraction of inspired oxygen (FiO2) to the patient from an oxygen delivery system;
    determining a percentage of oxygen saturation of blood hemoglobin (SpO2) of the patient and reporting the measured SpO2 at the oxygen delivery system;
    calculating a ratio of SpO2 to FiO2 ($S/_{CLC}F$ ratio); and
    automatically adjusting at the oxygen delivery system the FiO2 provided to the patient using the measured SpO2 and the calculated $S/_{CLC}F$ ratio to maintain SpO2 within a desired range; and
    graphing the $S/_{CLC}F$ ratio, and one or both of measured SpO2 and the calculated rate of change of the $S/_{CLC}F$ ratio, as a function of time.

18. The method of claim 17, further comprising graphing the measured SpO2 and the calculated rate of change of the $S/_{CLC}F$ ratio as a function of time.

19. The method of claim 17, wherein the desired range is from 88% to 95%.

20. The method of claim 17, further comprising issuing an alert from the oxygen delivery system when the $S/_{CLC}F$ ratio falls below a predetermined threshold.

21. The method of claim 20, wherein the predetermined threshold comprises 250.

22. The method of claim 20, further comprising intubating the patient in response to the alert.

23. The method of claim 17, wherein the FiO2 is provided to the patient by a tube.

24. The method of claim 17, wherein the FiO2 is provided to the patient by a mask.

25. The method of claim 17, wherein the FiO2 is provided to the patient by a chamber.

26. The method of claim 17, wherein the oxygen delivery system is configured to be portable and is carried to the patient.

27. The method of claim 17, wherein the method is used in a home of the patient.

28. The method of claim 17, further comprising continually adjusting a pressure at which the FiO2 is provided to the patient.

29. The method of claim 17, further comprising wirelessly transmitting to an external device any one or more of SpO2, the $S/_{CLC}F$ ratio, and a calculated rate of change of the $S/_{CLC}F$ ratio, as a function of time.

30. The method of claim 17, wherein the FiO2 provided to the patient is increased if the $S/_{CLC}F$ ratio falls below a predetermined threshold value.

31. The method of claim 30, wherein the predetermined threshold value is 300, 200, 250, or 100.

32. The method of claim 30, wherein the predetermined threshold value is 250.

33. The method of claim 17, wherein adjusting the FiO2 provided to the patient comprises increasing or initiating PEEP, increasing or initiating positive or negative pressure, or increasing tidal volume.

34. The method of claim 17, wherein the patient has acute respiratory distress syndrome.

35. The method of claim 17, wherein the patient has suffered a traumatic injury.

36. The method of claim 17, wherein the patient has chronic obstructive pulmonary disease (COPD).

37. The method of claim 17, wherein the patient has congestive heart failure (CHF).

38. The method of claim 17, wherein the method is performed on the patient after being anesthetized.

39. The method of claim 17, wherein the method is performed after the patient has been extubated.

40. The method of claim 17, wherein the patient is a neonate.

* * * * *